(12) United States Patent
Torgerson et al.

(10) Patent No.: US 8,989,869 B2
(45) Date of Patent: *Mar. 24, 2015

(54) BATTERY RECHARGE MANAGEMENT FOR IMPLANTABLE MEDICAL DEVICE

(75) Inventors: Nathan A. Torgerson, Andover, MN (US); James E. Riekels, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/959,138

(22) Filed: Dec. 2, 2010

(65) Prior Publication Data

US 2011/0077720 A1    Mar. 31, 2011

Related U.S. Application Data

(60) Continuation of application No. 11/641,263, filed on Dec. 19, 2006, now Pat. No. 7,865,245, which is a division of application No. 09/562,221, filed on Apr. 28, 2000, now Pat. No. 7,167,756.

(51) Int. Cl.
*A61N 1/365* (2006.01)
*A61N 1/378* (2006.01)

(52) U.S. Cl.
CPC .................................. *A61N 1/3787* (2013.01)
USPC .......................................................... 607/61

(58) Field of Classification Search
CPC .... A61N 1/3787; Y02E 60/12; Y02E 60/122; H02J 7/0068; H02J 7/007; H02J 7/0077; H02J 7/0081; H02J 7/0083; H02J 7/0085; H02J 7/0086; H02J 7/009; H02J 7/00918; H01M 10/44; H01M 10/443; H01M 10/445; H01M 10/446; H01M 10/448; G01R 31/3648

USPC ....................... 320/128, 130, 132; 607/60, 61
See application file for complete search history.

(56) References Cited

U.S. PATENT DOCUMENTS 4,080,558 A    3/1978    Sullivan et al.
4,232,679 A    11/1980    Schulman
(Continued)

FOREIGN PATENT DOCUMENTS

EP    0 619 123 A2    4/1994
JP    640662    3/1994
(Continued)

OTHER PUBLICATIONS

International Search Report for PCT Application PCT/US01/01694.
(Continued)

*Primary Examiner* — Christopher D Koharski
*Assistant Examiner* — Frances Oropeza
(74) *Attorney, Agent, or Firm* — IPLM Group, P.A.

(57) ABSTRACT

An implantable medical device having an implantable power source such as a rechargeable lithium ion battery. The implantable medical device includes a recharge module that regulates the recharging process of the implantable power source using closed-loop feedback control. The recharge module includes a recharge regulator, a recharge measurement device monitoring at least one recharge parameter, and a recharge regulation control unit for regulating the recharge energy delivered to the power source in response to the recharge measurement device. The recharge module adjusts the energy provided to the power source to ensure that the power source is being recharged under safe levels.

57 Claims, 6 Drawing Sheets

(56) References Cited

U.S. PATENT DOCUMENTS

| | | |
|---|---|---|
| 5,179,950 A | 1/1993 | Stanislaw |
| 5,344,431 A | 9/1994 | Merritt et al. |
| 5,354,320 A | 10/1994 | Schaldach et al. |
| 5,411,537 A * | 5/1995 | Munshi et al. ............ 607/33 |
| 5,733,313 A | 3/1998 | Barreras, Sr. et al. |
| 5,735,887 A | 4/1998 | Barreras, Sr. et al. |
| 5,749,909 A | 5/1998 | Schroeppel et al. |
| 5,752,977 A | 5/1998 | Grevious et al. |
| 5,807,397 A | 9/1998 | Barreras |
| 5,876,425 A | 3/1999 | Gord et al. |
| 5,941,906 A | 8/1999 | Barreras, Sr. et al. |
| 5,991,664 A | 11/1999 | Seligman |
| 5,991,665 A | 11/1999 | Wang et al. |
| 6,278,258 B1 | 8/2001 | Echarri et al. |
| 6,553,263 B1 * | 4/2003 | Meadows et al. ............ 607/61 |
| 7,865,245 B2 * | 1/2011 | Torgerson et al. ............ 607/61 |
| 2011/0077720 A1 * | 3/2011 | Torgerson et al. ............ 607/61 |

FOREIGN PATENT DOCUMENTS

| | | |
|---|---|---|
| JP | 965635 | 3/1997 |
| WO | WO 98/02040 | 1/1998 |
| WO | WO 98/11942 | 3/1998 |
| WO | WO 98/37926 | 9/1998 |
| WO | WO 99/06108 | 2/1999 |

OTHER PUBLICATIONS

European Search Report for EP 05016794.9.

* cited by examiner

INS ENVIRONMENT

BATTERY RECHARGE MANAGEMENT FOR IMPLANTABLE MEDICAL DEVICE

RELATED APPLICATION

This application is a continuation of and claims priority from U.S. patent application Ser. No. 11/641,263, filed Dec. 19, 2006, now U.S. Pat. No. 7,865,245, issued Jan. 4, 2011, which is a divisional of U.S. patent application Ser. No. 09/562,221, filed Apr. 28, 2000, now U.S. Pat. No. 7/167,756, issued Jan. 23, 2007.

This patent application is related to the following patents and patent applications:

U.S. patent application Ser. No. 09/561,566, entitled "Implantable Medical Pump with Multi-layer Back-up Memory," filed on Apr. 28, 2000, and having named inventors David C. Ullestad and Irfan Z. Ali (now U.S. Pat. No. 6,635,048, issued Oct. 21, 2003);

U.S. patent application Ser. No. 09/560,755, entitled "Power Management for an Implantable Medical Device," filed on Apr. 28, 2000, and having named inventors Nathan A. Torgerson and James E. Riekels (now U.S. Pat. No. 6,453,198, issued Sep. 17, 2002); and U.S. patent application Ser. No. 10/002,328, entitled "Method and Apparatus for Programming an Implantable Medical Device," filed Nov. 1, 2001 (now U.S. Pat. No. 7,187,978, issued Mar. 6, 2007).

FIELD OF INVENTION

This invention relates generally to implantable medical devices, and more particularly to a battery recharge management system for implantable medical devices.

DESCRIPTION OF THE RELATED ART

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

One type of implantable medical device is an Implantable Neuro Stimulator (INS). The INS delivers mild electrical impulses to neural tissue using an electrical lead. The neurostimulation targets desired neural tissue to treat the ailment of concern. For example, in the case of pain, electrical impulses (which are felt as tingling) may be directed to cover the specific sites where the patient is feeling pain. Neurostimulation can give patients effective pain relief and can reduce or eliminate the need for repeat surgeries and the need for pain medications.

Implantable medical devices such as neurostimulation systems may be partially implantable where a battery source is worn outside the patient's body. This system requires a coil and/or an antenna to be placed on the patient's skin over the site of the receiver to provide energy and/or control to the implanted device. Typically, the medical device is totally implantable where the battery is part of the implanted device. The physician and patient may control the implanted system using an external programmer. Such totally implantable systems include, for example, the Itrel® 3 brand neurostimulator sold by Medtronic, Inc. of Minneapolis, Minn.

In the case of an INS, for example, the system generally includes an implantable neurostimulator (INS) (also known as an implantable pulse generator (IPG)), external programmer(s), and electrical lead(s). The INS is typically implanted near the abdomen of the patient. The lead is a small medical wire with special insulation. It is implanted next to the spinal cord through a needle and contains a set of electrodes (small electrical contacts) through which electrical stimulation is delivered to the spinal cord. The lead is coupled to the INS via an implanted extension cable. The INS can be powered by an internal source such as a battery or by an external source such as a radio frequency transmitter. The INS contains electronics to send precise, electrical pulses to the spinal cord, brain, or neural tissue to provide the desired treatment therapy. The external programmer is a hand-held device that allows the physician or patient to optimize the stimulation therapy delivered by the INS. The external programmer communicates with the INS using radio waves.

In totally implantable systems, it is desirable to efficiently and effectively recharge the implanted battery source. One such technique is the use of a replenishable, high capacitive power source as disclosed, for example, in U.S. Pat. No. 5,807,397. This reference is incorporated herein by reference in its entirety. These capacitive power sources require that they be replenished frequently, a daily or other periodic basis, via an external, RF coupled device. This frequent replenishment of the capacitive power source, however, gives rise to a host of disadvantages, such as the frequent and continuous need for an available external, RF coupled device to replenish the capacitive power source, as well as the inconvenience of frequent replenishment of the capacitive power source.

An alternative such rechargeable power source is a rechargeable battery, such as a lithium ion battery. The rechargeable battery provides a number of advantages over the capacitive power source including (1) less frequent replenishment; and (2) a smaller size and weight. Each of these advantages improves the quality of life of the patient. In this regard, U.S. Pat. No. 5,991,665 discloses an energy transfer system for transmitting energy to an implantable medical device. This reference is incorporated herein by reference in its entirety.

Although the rechargeable battery provides distinct advantages over the capacitive power source, care must be taken in the recharging process so as to maintain the battery's storage capacity and efficacy. For example, recharge of the battery at too high a voltage can damage the battery. Similarly, too high a recharge current can also be harmful to the battery. Damage may also result if the temperature of the INS increases significantly during recharge. Damage to the battery results in reduced efficacy, thereby requiring more frequent recharging, and even eventual replacement of the battery (by surgically explanting the INS). On the one hand, it is undesirable to overheat and damage the battery if it is charged too rapidly. On the other hand, however, it is desirable to charge the battery efficiently to minimize the charging time and improve patient quality of life.

Accordingly, it is desirable to provide a recharge management system for an implantable medical device that preserves the efficacy of the battery during recharge as well as provides efficient recharging of the battery.

SUMMARY OF THE INVENTION

In a preferred embodiment, the present invention is a recharge management system for an implantable medical device having a rechargeable power source such as a lithium ion battery, a recharge coil associated with the implantable device capable of receiving via telemetry magnetic recharge energy from an external device, a recharge regulator receiving the magnetic recharge energy from the recharge coil and providing the recharge energy to the rechargeable power source, a recharge measurement device monitoring at least one recharge parameter, and a recharge regulation control unit for regulating the recharge energy delivered to the power source in response to the recharge measurement device. The recharge measurement device measures voltage and current levels being delivered by the external source, voltage and current levels being delivered to the power source, and the energy level of the power source. These measurements are provided to the recharge regulation control unit to adjust the energy provided to the power source to ensure that the power source is being recharged under safe levels. The temperature of the implantable medical device is also monitored. The recharge management system may further include an overvoltage protection circuit to limit the recharge energy delivered to the recharge regulator from the recharge coil and an AC to DC converter for converting the recharge energy from the recharge coil.

The present invention may be implemented within any number of implantable medical devices that require a self-contained rechargeable power source including, but not limited to, an implantable signal generator, an implantable drug pump, a pacemaker, a defibrillator, a cochlear implant, and an implantable diagnostic device.

DESCRIPTION OF THE PREFERRED EMBODIMENTS

The entire content of U.S. patent application Ser. No. 11/641,263, filed Dec. 12, 2006 now U.S. Pat. No. 7,865,245, issued Jan. 4, 2011, and U.S. patent application Ser. No. 09/562,221, filed Apr. 28, 2000, now U.S. Pat. No. 7/167,756, issued Jan. 23, 2007, is hereby incorporated by reference.

The present invention is a battery recharge management system and method for an implantable medical device. The recharge management system regulates the recharge energy that is provided to the battery during recharge by limiting the current into the battery, ensuring against overcharging of the battery, ensuring a minimum and a maximum input voltage during recharge, and ensuring against overheating of the implantable medical device. In the preferred embodiment, the present invention is implemented within an implantable neurostimulator, however, those skilled in the art will appreciate that the present invention may be implemented generally within any implantable medical device having an implanted rechargeable battery including, but not limited to, implantable drug delivery devices, implantable devices providing stimulation and drug delivery, pacemakers, defibrillators, cochlear implants, and implantable diagnostic devices for detecting bodily conditions of certain organs, like the brain or the heart.

Figure 1:
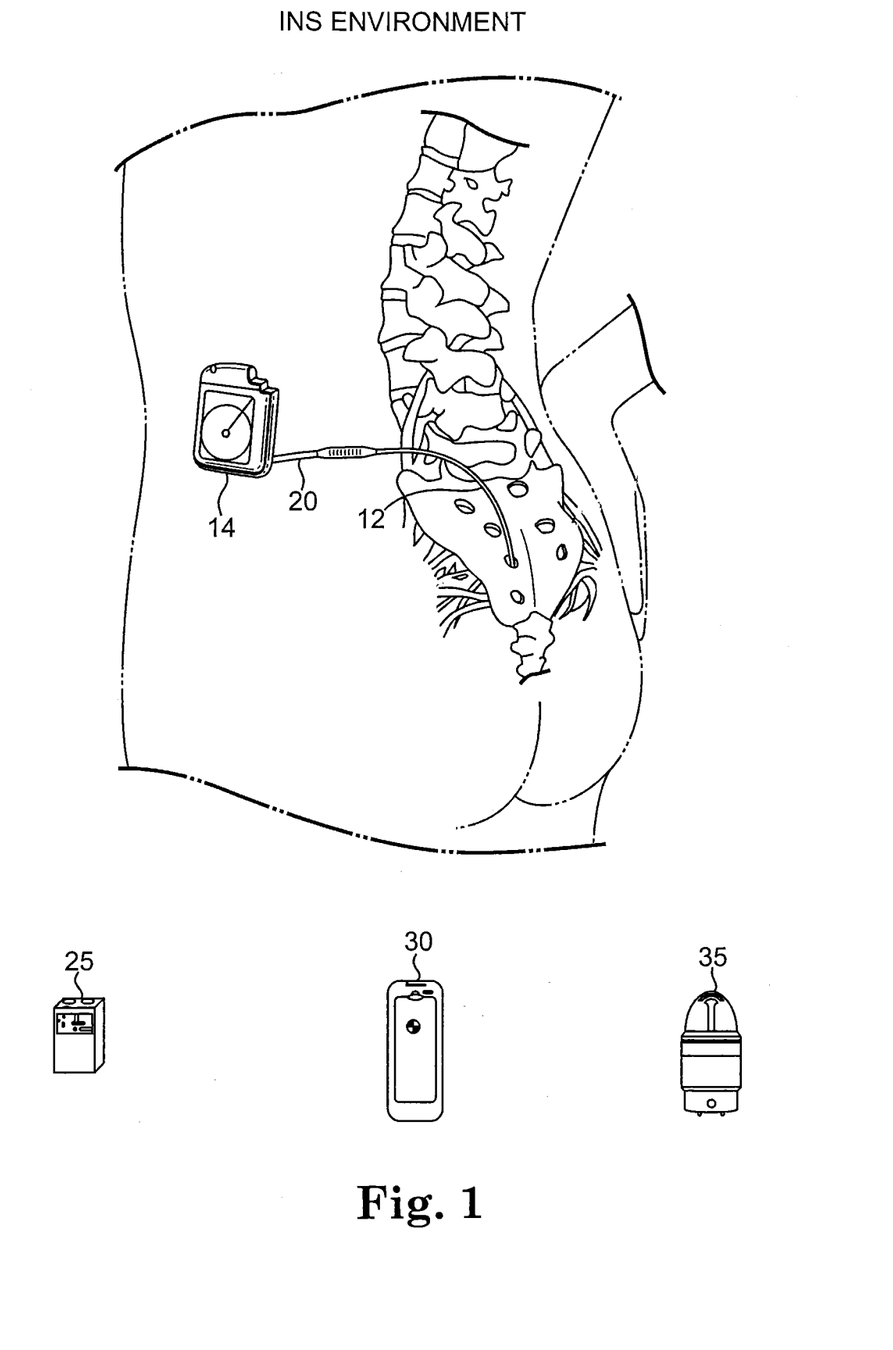
FIG. 1 illustrates an implantable medical device in accordance with a preferred embodiment of the present invention, as implanted in a human body.

FIG. 1 shows the general environment of an Implantable Neuro Stimulator (INS) medical device 14 in accordance with a preferred embodiment of the present invention. The neurostimulation system generally includes an INS 14, a lead 12, a lead extension 20, an External Neuro Stimulator (ENS) 25, a physician programmer 30, and a patient programmer 35. The INS 14 preferably is a modified implantable pulse generator that will be available from Medtronic, Inc. with provisions for multiple pulses occurring either simultaneously or with one pulse shifted in time with respect to the other, and having independently varying amplitudes and pulse widths. The INS 14 contains a power source 315 and electronics to send precise, electrical pulses to the spinal cord, brain, or neural tissue to provide the desired treatment therapy. As preferred, INS 14 provides electrical stimulation by way of pulses although other forms of stimulation may be used such as continuous electrical stimulation.

The lead 12 is a small medical wire with special insulation. The lead 12 includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 12 may also be a paddle having a plurality of electrodes including, for example, a Medtronic paddle having model number 3587A. In yet another embodiment, the lead 12 may provide electrical stimulation as well as drug infusion. Those skilled in the art will appreciate that any variety of leads may be used to practice the present invention.

The lead 12 is implanted and positioned to stimulate a specific site in the spinal cord or the brain. Alternatively, the lead 12 may be positioned along a peripheral nerve or adjacent neural tissue ganglia like the sympathetic chain or it may be positioned to stimulate muscle tissue. The lead 12 contains one or more electrodes (small electrical contacts) through which electrical stimulation is delivered from the INS 14 to the targeted neural tissue. If the spinal cord is to be stimulated, the lead 12 may have electrodes that are epidural, intrathecal or placed into the spinal cord itself Effective spinal cord stimulation may be achieved by any of these lead placements.

Although the lead connector can be connected directly to the INS 14, typically the lead connector is connected to a lead extension 20 which can be either temporary for use with an ENS 25 or permanent for use with an INS 14. An example of the lead extension 20 is Model 7495 available from Medtronic.

The ENS 25 functions similarly to the INS 14 but is not designed for implantation. The ENS 25 is used to test the efficacy of stimulation therapy for the patient before the INS 14 is surgically implanted. An example of an ENS 25 is a Model 3625 Screener available from Medtronic.

The physician programmer 30, also known as a console programmer, uses telemetry to communicate with the implanted INS 14, so a physician can program and manage a patient's therapy stored in the INS 14 and troubleshoot the patient's INS system. An example of a physician programmer 30 is a Model 7432 Console Programmer available from Medtronic. The patient programmer 35 also uses telemetry to communicate with the INS 14, so the patient can manage some aspects of her therapy as defined by the physician. An example of a patient programmer 35 is a Model 7434 Itrel® 3 EZ Patient Programmer available from Medtronic.

Those skilled in the art will appreciate that any number of external programmers, leads, lead extensions, and INSs may be used to practice the present invention.

Implantation of an Implantable Neuro Stimulator (INS) typically begins with implantation of at least one stimulation lead 12 usually while the patient is under a local anesthetic. The lead 12 can either be percutaneously or surgically implanted. Once the lead 12 has been implanted and positioned, the lead's distal end is typically anchored into position to minimize movement of the lead 12 after implantation. The lead's proximal end can be configured to connect to a lead extension 20. If a trial screening period is desired, the temporary lead extension 20 can be connected to a percutaneous extension with a proximal end that is external to the body and configured to connect to an External Neuro Stimulator (ENS) 25. During the screening period the ENS 25 is programmed with a therapy and the therapy is often modified to optimize the therapy for the patient. Once screening has been completed and efficacy has been established or if screening is not desired, the lead's proximal end or the lead extension proximal end is connected to the INS 14. The INS 14 is programmed with a therapy and then implanted in the body typically in a subcutaneous pocket at a site selected after considering physician and patient preferences. The INS 14 is implanted subcutaneously in a human body and is typically implanted near the abdomen of the patient.

Figure 2A:
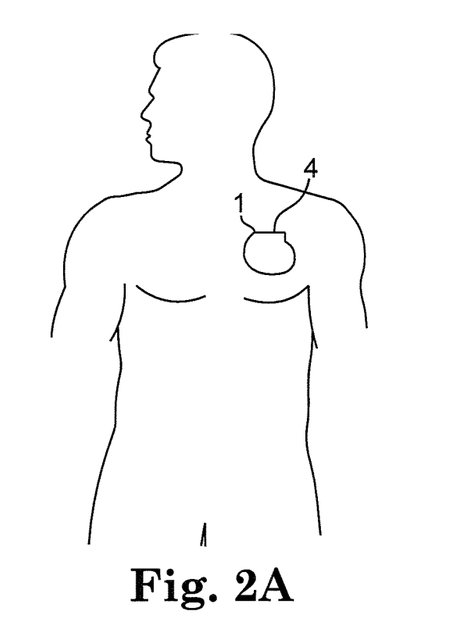
FIGS. 2A-D illustrates locations where the implantable medical device of the present invention can be implanted in the human body other than the location shown in FIG. 1.
Figure 2B:
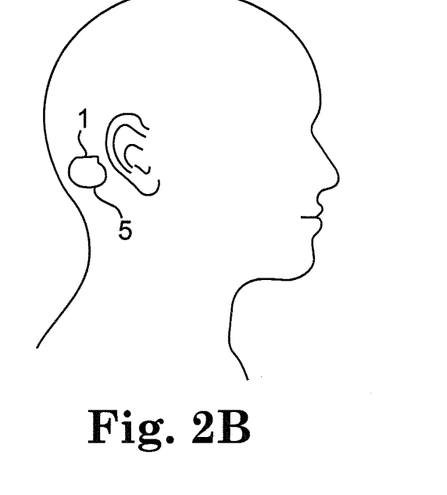
Figure 2C:
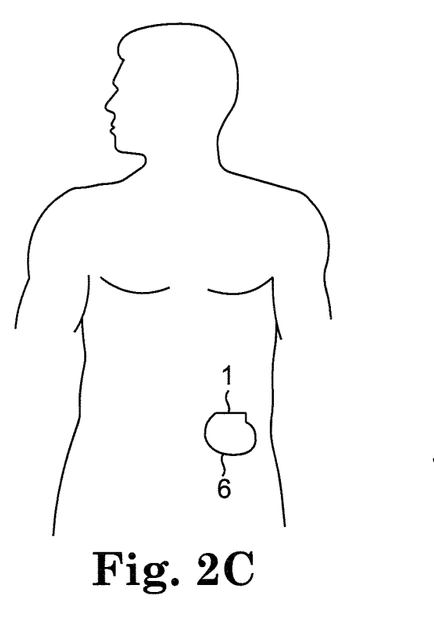
Figure 2D:
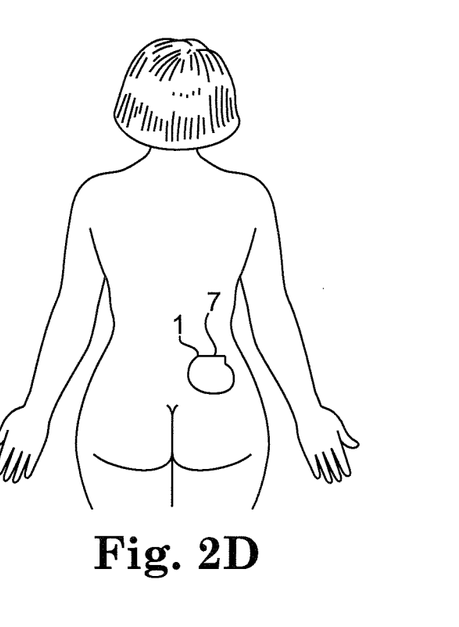

The above preferred embodiment for the placement of the INS 14 within the lower left abdominal region 6 of the patient is further illustrated in FIG. 2C. Other preferred embodiments for the placement of stimulator 1 within a human patient is further shown in FIGS. 2A, 2B, and 2D. As shown in FIG. 2A, the INS 14 can be implanted in a pectoral region 4 of the patient. As shown in FIG. 2B, the INS 14 can be implanted in a region 5 behind the ear of a patient, and more specifically in the mastoid region. As shown in FIG. 2D, the INS 14 can be placed in the lower back or upper buttock region 7 of the patient. The INS 14 is discussed in further detail herein.

The physician periodically uses the physician programmer 30 to communicate with the implanted INS 14 to manage the patient therapy and collect INS data. The patient 360 (see FIG. 3) uses the patient programmer 35 to communicate with the implanted INS 14 to make therapy adjustment that have been programmed by the physician, recharge the INS power source 315, and record diary entries about the effectiveness of the therapy. Both the physician programmer 30 and patient programmer since a fixed date for date/time stamping of events and for therapy control such as circadian rhythm linked therapies. The memory 340 includes memory sufficient for operation of the INS 14 such as volatile Random Access Memory (RAM) for example Static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as the telemetry module 305, so the telemetry module 305 can request control of the data bus 327 and write data directly to memory 340 bypassing the processor 335. The system reset 345 controls operation of ASICs and modules during power-up of the INS 14, so ASICs and modules registers can be loaded and brought on-line in a stable condition.

Figure 3:
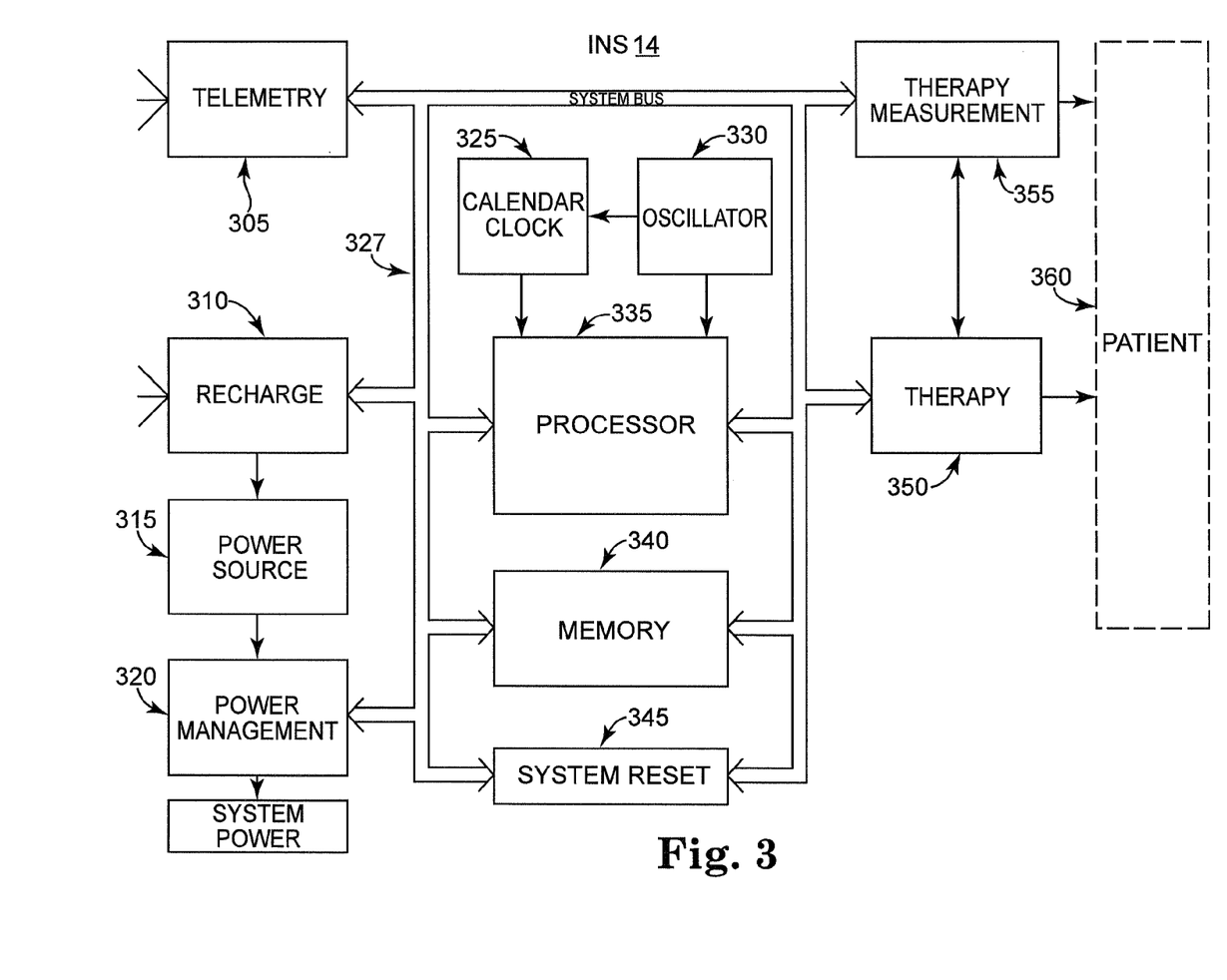
FIG. 3 is a schematic block diagram of an INS in accordance with a preferred embodiment of the present invention.

The telemetry module 305 provides bi-directional communications between the INS 14 and the external programmers 30 or 35. The telemetry module 305 generally comprises a telemetry antenna, a receiver, a transmitter, and a telemetry processor 335. Telemetry modules are generally known in the art and are further detailed in U.S. Pat. No. 5,752,977, entitled "Efficient High Data Rate Telemetry Format For Implanted Medical Device" issued to Grevious et al. (May 19, 1998), which is incorporated herein by reference in its entirety.

Those skilled in the art will appreciate that the INS 14 may be configured in a variety of versions by removing modules not necessary for the particular configuration and by adding additional components or modules. All component of the INS 14 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones.

Figure 4:
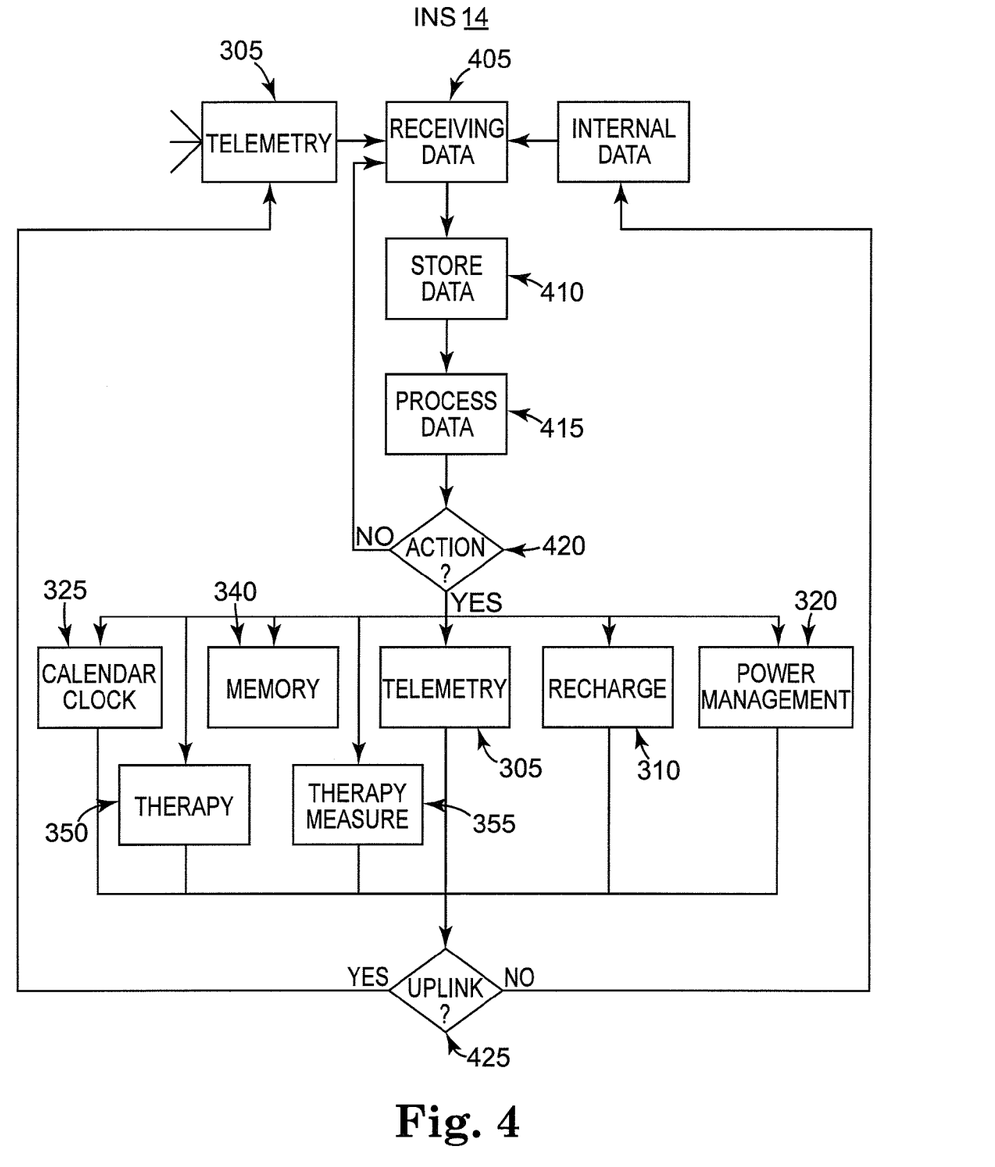
FIG. 4 depicts a general operation flowchart of the INS 14 in accordance with a preferred embodiment of the present invention.

FIG. 4 depicts a general operation flowchart of the INS 14. At step 405, operation of the INS 14 begins with the processor 335 receiving data from either telemetry module 305 or from an internal source in the INS 14. At step 410, the received data is stored in a memory location. At step 415, the data is processed by the processor 335 to identify the type of data and can include further processing such as validating the integrity of the data. At step 420, after the data is processed, a decision is made whether to take an action. If no action is required, the INS 14 stands by to receive data. If an action is required, the action will involve one or more of the following modules or components: calendar clock 325, memory 340, telemetry 305, recharge 310, power management 320, therapy 350, and therapy measurement 355. An example of an action would be to recharge the power source 315. At step 425, after the action is taken, a decision is made whether the action is to be communicated or "uplinked" to a patient or physician programmer 35 or 30 through the telemetry module 305. If the action is uplinked, the action is recorded in the patient or physician programmer. If the action is not uplinked, the action is recorded internally within the INS 14.

Figure 5:
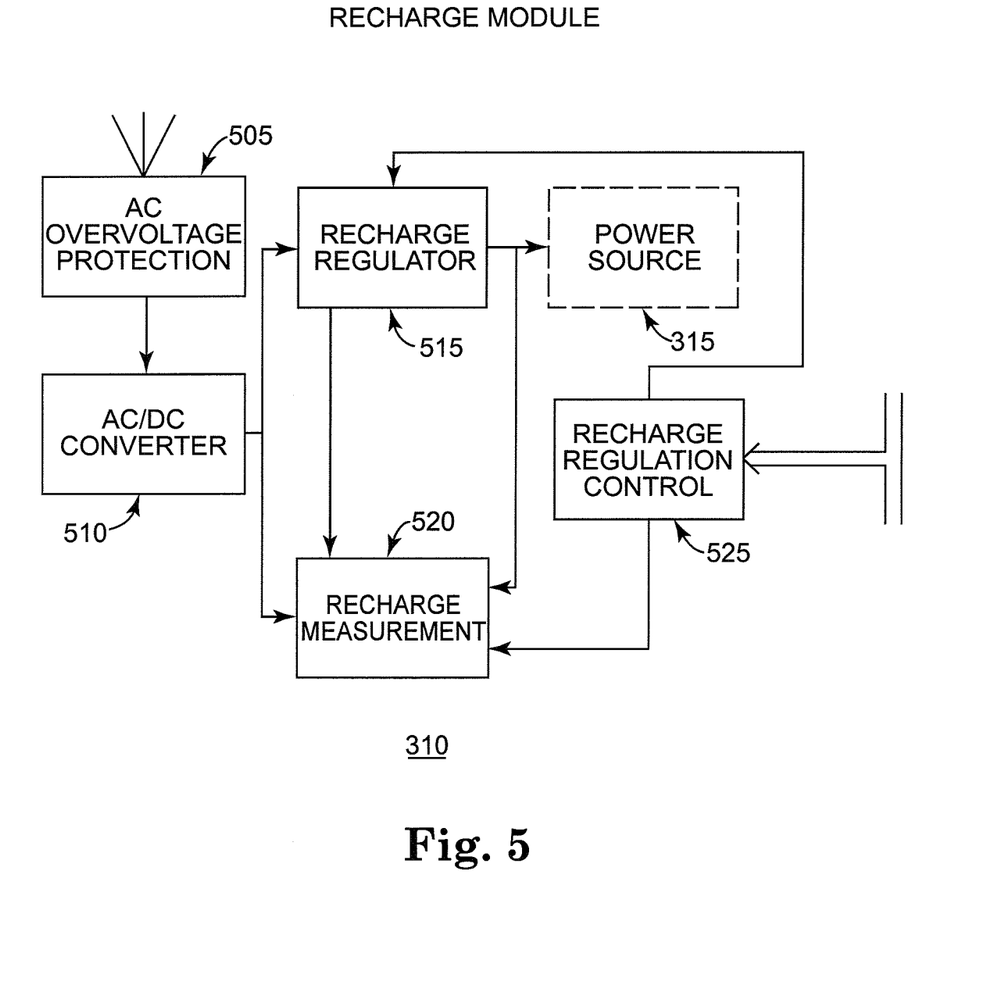
FIG. 5 is a schematic block diagram of the recharge module in accordance with a preferred embodiment of the present invention.

FIG. 5 is a schematic block diagram of the recharge module 310 of the INS 14 in accordance with a preferred embodiment of the present invention. The recharge module 310 provides a form of closed-loop feedback control to ensure proper and efficient charging of the battery with minimized risk of damage to the battery. The recharge module 310 serves to regulate the charging rate of the power source 315 according to power source parameters. The recharge module 310 also serves to maintain INS 14 temperature within acceptable limits so any temperature rise during recharge does not create an unsafe condition for the patient. The INS 14 communicates charging status to the patient charger, so the patient charges at optimum efficiency and at a level that prevents the INS 14 from overheating yet charges the power source 315 efficiently.

The recharge module 310 generally comprises a recharge coil, an Alternating Current (AC) over-voltage protection device 505, an AC to DC converter 510, a recharge regulator 515, a recharge measurement device 520, and a recharge regulation control unit 525. The recharge module 310 charges the battery by receiving an energy transfer signal with a frequency of about 5.0 KHz to 10.0 KHz and converting the energy transfer signal into a regulated DC power to charge the INS power source 315. The recharge coil can be the same coil as the telemetry antenna if multiplexed or the recharge coil can be separate from the telemetry antenna. The recharge coil may be within the INS 14 housing or may be outside the INS 14 housing but connected through a cable. The AC overvoltage protection device 505 can be a Zener diode that shunts high voltage to ground and may be placed at the input or output of the AC to DC converter 510. The AC to DC converter 510 can be a standard rectifier circuit or an active rectifier having integrated or discrete component designs.

The recharge regulator 515 regulates the voltage received from the AC to DC converter 510 to a level appropriate for charging the power source 315. The recharge regulation control unit 525 adjusts the recharge regulator 515 in response to information from the recharge measurement device 520 and a recharge program. The recharge program is generally within the INS memory 340 and can vary based upon the type of device, type of power source 315, and condition of the power source 315. The recharge measurement device 520 measures various recharge parameters of the INS 14 including, but not limited to, the input and output voltage at the recharge regulator 515, the input and output current at the recharge regulator 515, input voltage to the power source, input current to the power source, power source voltage, and power source charge. The recharge measurement device 520 also measures temperature of the INS 14. For example, temperature of specific areas of the INS 14 may be measured including, but not limited to, the recharge coil, recharge regulator 515, power source 315, and the outer shield for the INS 14. Based upon the recharge measurement, the recharge regulation control unit 525 can increase or decrease the energy reaching the power source 315 (discussed herein).

Advantageously, the recharge method and apparatus of the present invention supplies a regulated voltage and current to the rechargeable power source 315. The regulated voltage and current is continually monitored during recharge. As preferred, the charge current will be controlled to be within the range of 0-100 mA, with capability to achieve 150-200 mA. During recharge under controlled current, voltage is monitored. As preferred the charge voltage will be controlled to be in the range of 50 mV-5.0 V with a maximum being in the range of 6.0 V. During recharge under controlled voltage, the current supply is monitored and tapered to prevent the risk of damage to the power source 315. Further, the temperature sensing may further limit the charge current threshold in the case of more than a certain rise in temperature in the INS 14. Moreover, the recharge module 310 protects the power source 315 from sudden bursts of energy from an outside source, known or unknown. Even further, the present invention provides for more efficient recharge, namely provides information as to whether recharging energy can be gradually increased to more efficiently recharge the power source 315. Still further, the INS 14 continues to deliver therapy during the recharge process without affecting the stimulation pulse.

Figure 6:
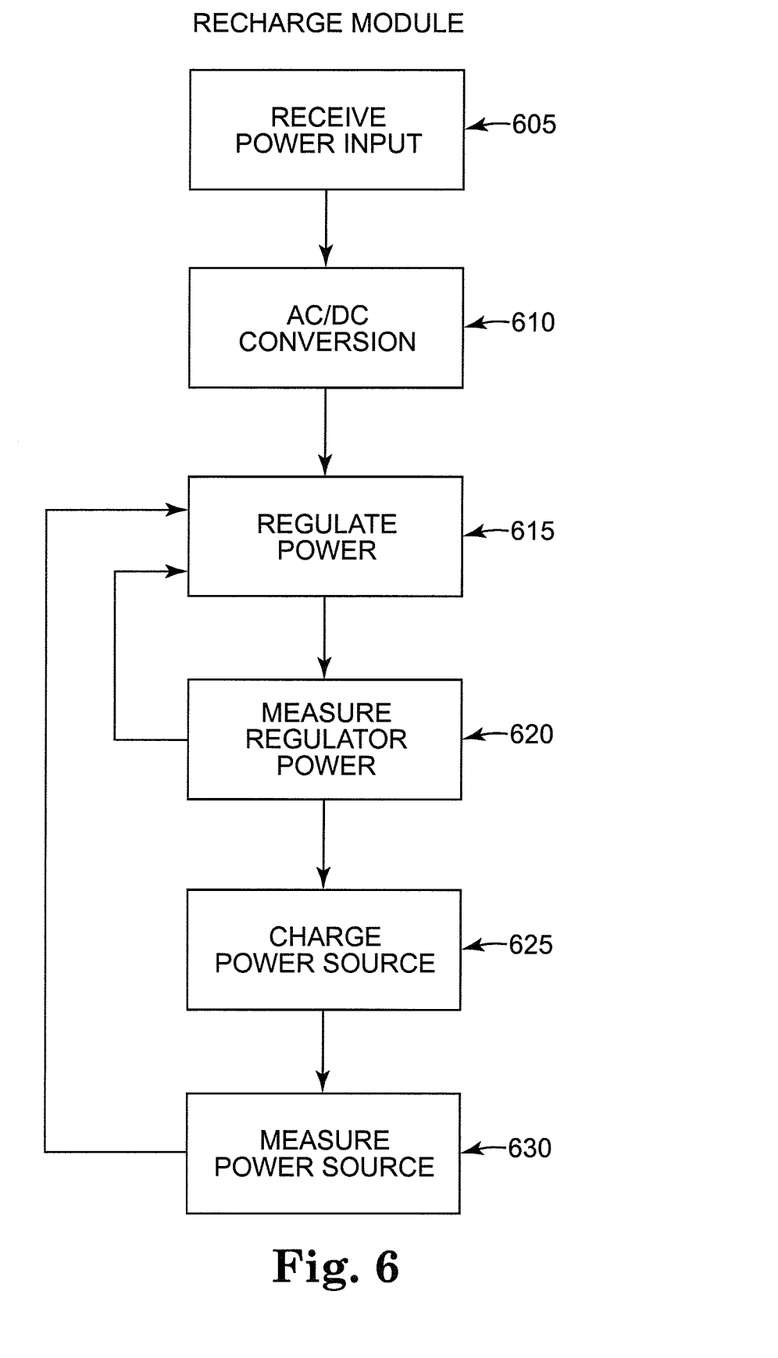
FIG. 6 is a flow chart depicting the operation of the recharge module 310 in accordance with a preferred embodiment of the present invention.

FIG. 6 is a flow chart depicting the operation of the recharge module 310 in accordance with a preferred embodiment of the present invention. This process may be stored as a recharge program that is run by processor 335 and stored in memory 340. At step 605, the recharging process for the INS 14 begins with the patient or the physician, using an external patient programmer 35 or physician programmer 30, placing a telemetry head containing the recharge coil near the INS 14. Both the patient and physician programmers 30 and 35 have an antenna or coil locator that indicates when the telemetry head is aligned closely enough with the implanted INS 14 for adequate telemetry and charge coupling. A coil (not shown) of the external component creates a magnetic field that a coil of the INS 14 receives. The external component also emits command signals to the antenna of the INS 14. These received command signals are demodulated (step 610) by the telemetry unit 305 and communicated to the processor 335. The processor 335 activates the proper control for the inductor to receive the RF coupled energy from the inductor of the external component. The magnetic recharge energy may then be delivered from the external programmers 30 or 35 to the INS 14.

In the event that the power source 315 is almost depleted of energy, the power source 315 may not have sufficient energy to provide the feedback control. In this event, the external component may deliver an initial large burst of energy to "wake up" the power source 315 and the 315 is replenished to a maximum voltage; (3) the charge current to the power source 315 $I_{in}$ reaches a maximum limit; or (4) the temperature increases more than a preset amount.

In steps 615, 620 and 625, recharge regulation control unit 525 provides feedback as to whether the power source 315 is receiving the recharge energy and whether the recharge energy is too high or too low. If the recharge energy is too high, the energy can be reduced to reduce risk of damage to the power source 315. If the recharge energy is too low, it can be slowly increased to improve recharge efficiency. This can be achieved by adjusting the recharge energy that the recharge regulator 515 provides to the power source 315 and/or by notifying the external component via telemetry signaling to increase or decrease the delivery of magnetic recharge energy. The recharge regulation control unit 525 communicates with the external component via telemetry unit 305. Those skilled in the art will appreciate that other communication techniques may be implemented. For example, the recharge regulation control unit 525 communicates with the external component by modulating the load on the recharge coil. This change in the load can then be sensed in the circuitry driving the source coil of the external component.

If the current or voltage being supplied to the power source 315 is too high, the recharge regulation control unit 525 will regulate the current down. The next time the INS 14 communicates to the external charging device, it will inform the charging device that the RF energy being sent is higher than necessary and the charging device will adjust its RF transmission of energy accordingly. Likewise, the INS 14 will communicate to the charging device to lower the supplied energy if components in the INS 14 are heating up above safe limits for the patent and/or device. Similarly, if the temperature is safe and the current and voltage levels are below the charge rate capacity of the power source 315, the INS 14 will communicate to the charging device that the RF energy can be increased.

At step 630, the recharge measurement unit 520 measures the power source 315 and provides this information to the recharge regulation control unit 525 to control the recharge regulator output energy to an appropriate energy level. Once the power source 315 is fully charged, the recharge regulation control unit 525 instructs the recharge regulator 515 to stop delivery of recharge energy to the power source 315. Optionally, a signal may also be provided via telemetry unit 305 notifying the external device that the power source 315 is fully recharged.

Alternative procedures for halting the charging process may also be used. For example, the processor 335 may be coupled to the charge/discharge monitor. The charge/discharge monitor may notify the processor 335 that a "fully charged" state is reached in the rechargeable power source 315. When the processor 335 determines that a "fully charged" state is reached in the rechargeable power source 315, the processor 335 may then send a signal via the telemetry unit 305 and onto the external component. Upon receipt of this command signal, the external component may turn off the energy transmitted to the inductor.

During the recharge process, operation of various INS 14 components that was previously suspended due to low battery energy is resumed. This aspect is detailed further in U.S. patent application Ser. No. 09/560,755 filed Apr. 28, 2000 (now U.S. Pat. No. 6,453,198, issued Sep. 17, 2002), entitled "Power Management for an Implantable Medical Device," having the same inventive entity as that of the present patent application. This co-pending patent application is incorporated herein by reference in its entirety.

In alternative embodiments, the battery recharge management system of the present invention can be used with any other implantable systems requiring a self-contained rechargeable power source, including, but not limited to, pacemakers, defibrillators, and cochlear implants. In another alternative embodiment, the battery recharge management system of the present invention may also be used to recharge an implantable diagnostic device for detecting bodily conditions of certain organs, like the brain or the heart. In yet another alternative embodiment, the battery recharge management system of the present invention can be used to recharge a drug delivery system having an implantable battery-powered pump.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

What is claimed is:

1. A recharge management system for an implantable medical device, comprising in combination:
a rechargeable power source operatively coupled with the implantable medical device;
a recharge coil operatively coupled with the implantable medical device and being capable of receiving energy from an external device to recharge the rechargeable power source;
a recharge measurement device configured to monitor a temperature; and
a recharge regulation control unit configured to regulate a charging rate of the rechargeable power source by increasing the charging rate, at least in part, in response to the temperature monitored by the recharge measurement device.

2. The recharge management system of claim 1 wherein the recharge measurement device further monitors a temperature of a component of an implantable medical device.

3. The recharge management system of claim 2 wherein the recharge regulation control unit increases the charging rate if the temperature is safe and a current level and a voltage level of the rechargeable power source are below a charge rate capacity of the rechargeable power source.

4. The recharge management system of claim 1 wherein the recharge management device further monitors a temperature component of the implantable medical device.

5. The recharge management system of claim 1 wherein the recharge regulation control unit also being capable of decreasing the charging rate in response to the input voltage and the temperature monitored by the recharge measurement device.

6. The recharge management system of claim 1 wherein the recharge regulation control unit initially provides a relative low charging rate and subsequently increases the charging rate.

7. The recharge management system of claim 1 wherein the recharge regulation control unit increases the charging rate to improve recharge efficiency.

8. The recharge management system of claim 7 wherein the recharge regulation control unit decreases the charging rate to reduce risk of damage to the rechargeable power source.

9. The recharge management system of claim 7 wherein the recharge regulation control unit decreases the charging rate if components of the implantable medical device are heating up above safe limits.

10. The recharge management system of claim 1, further comprising a telemetry unit providing communication between the external device and the recharge regulation control unit to adjust the charging rate provided by the external device.

11. The recharge management system of claim 1, further comprising:
a recharge regulator receiving the energy from the recharge coil and providing the energy to the rechargeable power source.

12. The recharge management system of claim 1 wherein the recharge measurement device is configured to monitor a temperature of the implantable medical device.

13. The recharge management system of claim 1 wherein the recharge measurement device is implantable.

14. The recharge management system of claim 1 wherein the recharge regulation control unit is implantable.

15. The recharge management system of claim 1 wherein the recharge measurement device and the recharge regulation control unit are implantable.

16. The recharge management system of claim 1 wherein the recharge measurement device is configured to monitor the temperature of the recharge coil and wherein the recharge regulation control unit is configured to regulate the charging rate of the rechargeable power source by increasing the charging rate, at least in part, in response to the temperature of the recharge coil.

17. The recharge management system of claim 1 wherein the recharge measurement device is configured to monitor the temperature of the recharge regulation control unit and wherein the recharge regulation control unit is configured to regulate the charging rate of the rechargeable power source by increasing the charging rate, at least in part, in response to the temperature of the recharge regulation control unit.

18. The recharge management system of claim 1 wherein the recharge measurement device is configured to monitor the temperature of the rechargeable power source and wherein the recharge regulation control unit is configured to regulate the charging rate of the rechargeable power source by increasing the charging rate, at least in part, in response to the temperature of the rechargeable power source.

19. The recharge management system of claim 1 wherein the implantable medical device further comprises an outer shield and wherein the recharge measurement device is configured to monitor the temperature of the outer shield and wherein the recharge regulation control unit is configured to regulate the charging rate of the rechargeable power source by increasing the charging rate, at least in part, in response to the temperature of the outer shield.

20. A recharge management system for an implantable medical device, comprising in combination:
an external device providing a source of recharge energy;
a rechargeable power source operatively coupled with the implantable medical device;
a recharge coil operatively coupled with the implantable medical device and being capable of receiving energy from the external device to recharge the rechargeable power source;
a recharge measurement device configured to monitor a temperature; and
a recharge regulation control unit configured to regulate a charging rate of the rechargeable power source by increasing the charging rate, at least in part, in response to the temperature monitored by the recharge measurement device.

21. The recharge management system of claim 20 wherein the recharge measurement device further monitors a temperature of a component of an implantable medical device.

22. The recharge management system of claim 20 wherein the recharge regulation control unit increases the charging rate if the temperature is safe and a current level and a voltage level of the rechargeable power source are below a charge rate capacity of the rechargeable power source.

23. The recharge management system of claim 20 wherein the recharge management device further monitors a temperature component of the implantable medical device.

24. The recharge management system of claim 20 wherein the recharge regulation control unit also being capable of decreasing the charging rate in response to the input voltage and the temperature monitored by the recharge measurement device.

25. The recharge management system of claim 20 wherein the recharge regulation control unit initially provides a relatively low charging rate and subsequently increases the charging rate.

26. The recharge management system of claim 20 wherein the recharge regulation control unit increases the charging rate to improve recharge efficiency.

27. The recharge management system of claim 26 wherein the recharge regulation control unit decreases the charging rate to reduce risk of damage to the rechargeable power source.

28. The recharge management system of claim 26 wherein the recharge regulation control unit decreases the charging rate if components of the implantable medical device are heating up above safe limits.

29. The recharge management system of claim 20, further comprising a telemetry unit providing communication between the external device and the recharge regulation control unit to adjust the charging rate provided by the external device.

30. The recharge management system of claim 20, further comprising:
a recharge regulator receiving the energy from the recharge coil and providing the energy to the rechargeable power source.

31. The recharge management system of claim 20 wherein the recharge measurement device is configured to monitor a temperature of the implantable medical device.

32. The recharge management system of claim 20 wherein the recharge measurement device is implantable.

33. The recharge management system of claim 20 wherein the recharge regulation control unit is implantable.

34. The recharge management system of claim 20 wherein the recharge measurement device and the recharge regulation control unit are implantable.

35. The recharge management system of claim 20 wherein the recharge measurement device is configured to monitor the temperature of the recharge coil and wherein the recharge regulation control unit is configured to regulate the charging rate of the rechargeable power source by increasing the charging rate, at least in part, in response to the temperature of the recharge coil.

36. The recharge management system of claim 20 wherein the recharge measurement device is configured to monitor the temperature of the recharge regulation control unit and wherein the recharge regulation control unit is configured to regulate the charging rate of the rechargeable power source by increasing the charging rate, at least in part, in response to the temperature of the recharge regulation control unit.

37. The recharge management system of claim 20 wherein the recharge measurement device is configured to monitor the temperature of the rechargeable power source and wherein the recharge regulation control unit is configured to regulate the charging rate of the rechargeable power source by increasing the charging rate, at least in part, in response to the temperature of the rechargeable power source.

38. The recharge management system of claim 20 wherein the implantable medical device further comprises an outer shield and wherein the recharge measurement device is configured to monitor the temperature of the outer shield and wherein the recharge regulation control unit is configured to regulate the charging rate of the rechargeable power source by increasing the charging rate, at least in part, in response to the temperature of the outer shield.

39. A method of recharging a rechargeable power source operatively coupled within an implantable medical device using a recharge management system, comprising the steps of:
(a) receiving energy with a recharge coil within the implantable medical device from an external energy source associated with an external device;
(b) recharging the rechargeable power source with the energy;
(c) monitoring, with a recharge measurement device, a temperature; and
(d) regulating, with a recharge regulation control unit, the step of recharging in response to the step of monitoring by increasing a charging rate of the rechargeable power source in response, at least in part, on the temperature sensed in the monitoring step.

40. The method of recharging of claim 39 wherein the regulating step increases the charging rate if the temperature is safe and a current level and a voltage level of the rechargeable power source are below a charge rate capacity of the rechargeable power source.

41. The method of recharging of claim 39 wherein the regulating step initially provides a relatively low charging rate and subsequently increases the charging rate.

42. The method of recharging of claim 41 wherein the regulating step increases the charging rate to improve recharge efficiency.

43. The method of recharging of claim 42 wherein the regulating step decreases the charging rate to reduce risk of damage to the rechargeable power source.

44. The method of recharging of claim 42 wherein the regulating step decreases the charging rate if components of the implantable medical device are heating up above safe limits.

45. The method of recharging of claim 39 wherein the step of regulating increases the charging rate to improve recharge efficiency.

46. The method of recharging of claim 39 wherein the step of regulating reduces the charging rate to reduce the risk of damage to the rechargeable power source.

47. The method of recharging of claim 39 wherein the step of regulating reduces the charging rate to prevent overheating of the implantable medical device.

48. The method of recharging of claim 39 wherein the implantable medical device comprises a recharge regulator.

49. The method of claim 39 wherein the temperature in the monitoring step is a temperature of the implantable medical device.

50. The method of claim 39 wherein the temperature in the monitoring step is a temperature of a component of the implantable medical device.

51. The method of claim 39 wherein the monitoring step is accomplished internally.

52. The method of claim 39 wherein the regulating step is accomplished internally.

53. The method of claim 39 wherein the monitoring step and the regulating step are accomplished internally.

54. The method of claim 39 wherein the monitoring step monitors the temperature of the recharge coil and wherein the regulating step regulates the charging rate of the rechargeable power source by increasing the charging rate, at least in part, in response to the temperature of the recharge coil.

55. The method of claim 39 wherein the monitoring step monitors the temperature of the recharge regulation control unit and wherein the regulating step regulates the charging rate of the rechargeable power source by increasing the charging rate, at least in part, in response to the temperature of the recharge regulation control unit.

56. The method of claim 39 wherein the monitoring step monitors the temperature of the recharge measurement device and wherein the regulating step regulates the charging rate of the rechargeable power source by increasing the charging rate, at least in part, in response to the temperature of the recharge measurement device.

57. The method of claim 39 wherein the implantable medical device further comprises an outer shield and wherein the monitoring step monitors the temperature of the outer shield and wherein the regulating step regulates the charging rate of the rechargeable power source by increasing the charging rate, at least in part, in response to the temperature of the outer shield.

* * * * *